(12) United States Patent
Fujiwara

(10) Patent No.: US 12,409,081 B2
(45) Date of Patent: Sep. 9, 2025

(54) DISPOSABLE DIAPER AND METHOD FOR MANUFACTURING THE SAME

(71) Applicant: DAIO PAPER CORPORATION, Shikokuchuo Ehime (JP)

(72) Inventor: Yuka Fujiwara, Ehime (JP)

(73) Assignee: Daio Paper Corporation, Ehime (JP)

( * ) Notice: Subject to any disclaimer, the term of this patent is extended or adjusted under 35 U.S.C. 154(b) by 416 days.

(21) Appl. No.: 17/997,759

(22) PCT Filed: May 7, 2021

(86) PCT No.: PCT/JP2021/017546
§ 371 (c)(1),
(2) Date: Nov. 2, 2022

(87) PCT Pub. No.: WO2021/241169
PCT Pub. Date: Dec. 2, 2021

(65) Prior Publication Data
US 2023/0157908 A1    May 25, 2023

(30) Foreign Application Priority Data

May 26, 2020 (JP) .................................. 2020-091545

(51) Int. Cl.
*A61F 13/511* (2006.01)

(52) U.S. Cl.
CPC .................. *A61F 13/51113* (2013.01); *A61F 2013/51117* (2013.01)

(58) Field of Classification Search
CPC .............. A61F 13/511; A61F 13/51113; A61F 13/8405; A61F 13/15; A61F 13/49; A61F 2013/51117

(Continued)

(56) References Cited

U.S. PATENT DOCUMENTS 10,596,048 B2 *  3/2020  Sherlock .................. B04B 1/20
2006/0184150 A1   8/2006  Noel

FOREIGN PATENT DOCUMENTS

JP    2004255164 A    9/2004
JP    2007528742 A    10/2007
(Continued)

OTHER PUBLICATIONS

International Search Report for PCT/JP2021/017546, dated Jul. 6, 2021.

*Primary Examiner* — James D Sells
(74) *Attorney, Agent, or Firm* — Andrus Intellectual Property Law, LLP

(57) ABSTRACT

A disposable diaper includes: a top sheet constituting a use-side surface; a liquid impervious sheet disposed on a back surface side; and an absorbent element interposed therebetween. A moisturizing agent mainly containing glycerin is applied to the top sheet, an application region of the moisturizing agent is an exposed region that can be at least visually recognized directly from a use surface side in an unfolded state of the product, and the exposed region has high concentration application regions Q of the moisturizing agent in at least one of peripheral portions in a front-back direction and peripheral portions in a width direction, and a low concentration application region MZ of the moisturizing agent in an intermediate region between the high concentration application regions.

1 Claim, 14 Drawing Sheets

(58) Field of Classification Search
USPC .......................................................... 156/64
See application file for complete search history.

(56) References Cited

FOREIGN PATENT DOCUMENTS

| | | |
|---|---|---|
| JP | 2008529721 A | 8/2008 |
| JP | 2016013414 A | 1/2016 |
| JP | 5913889 | 4/2016 |
| JP | 2018102836 A | 7/2018 |
| WO | 2004080358 A1 | 9/2004 |

* cited by examiner

[FIG.1]
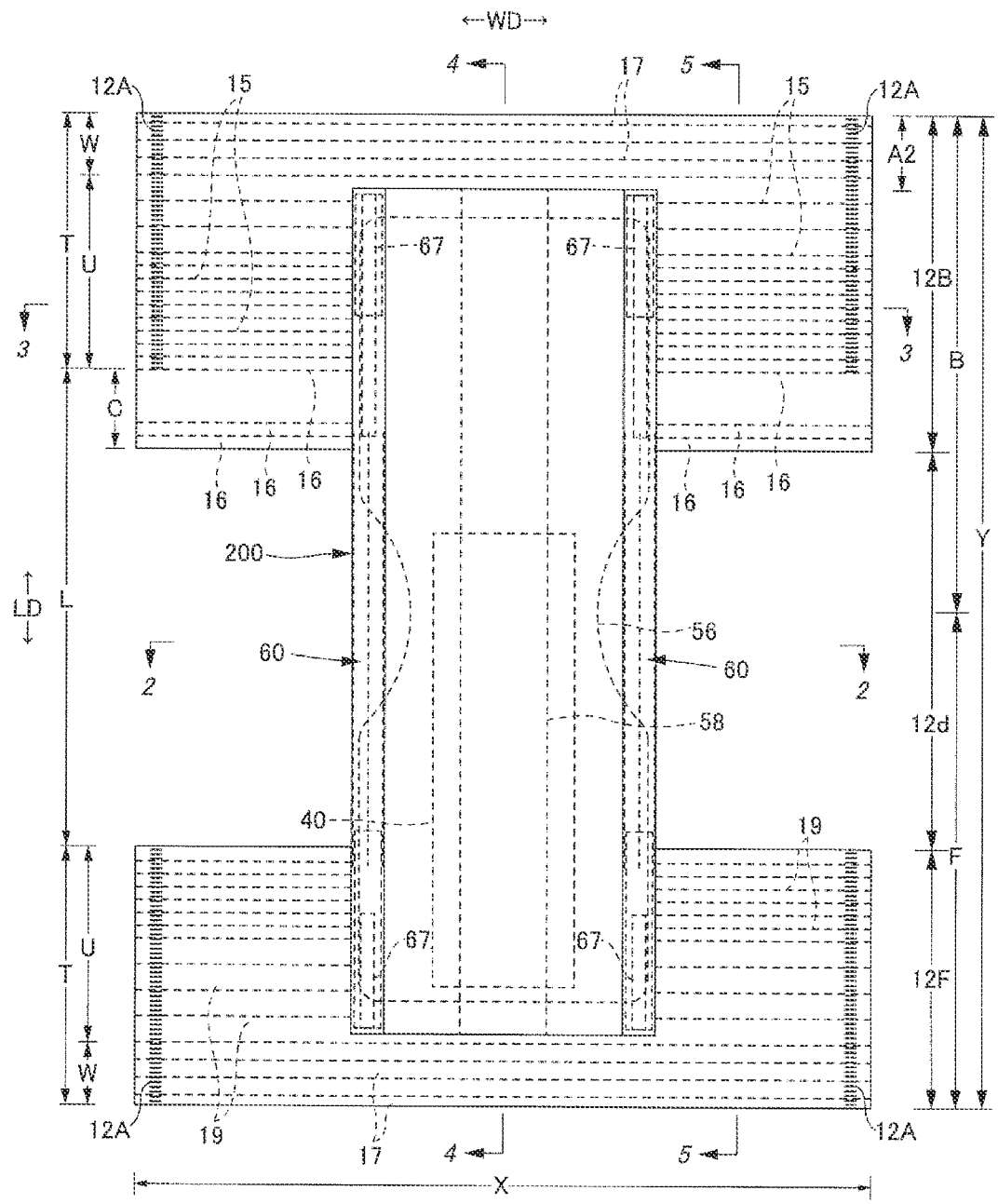

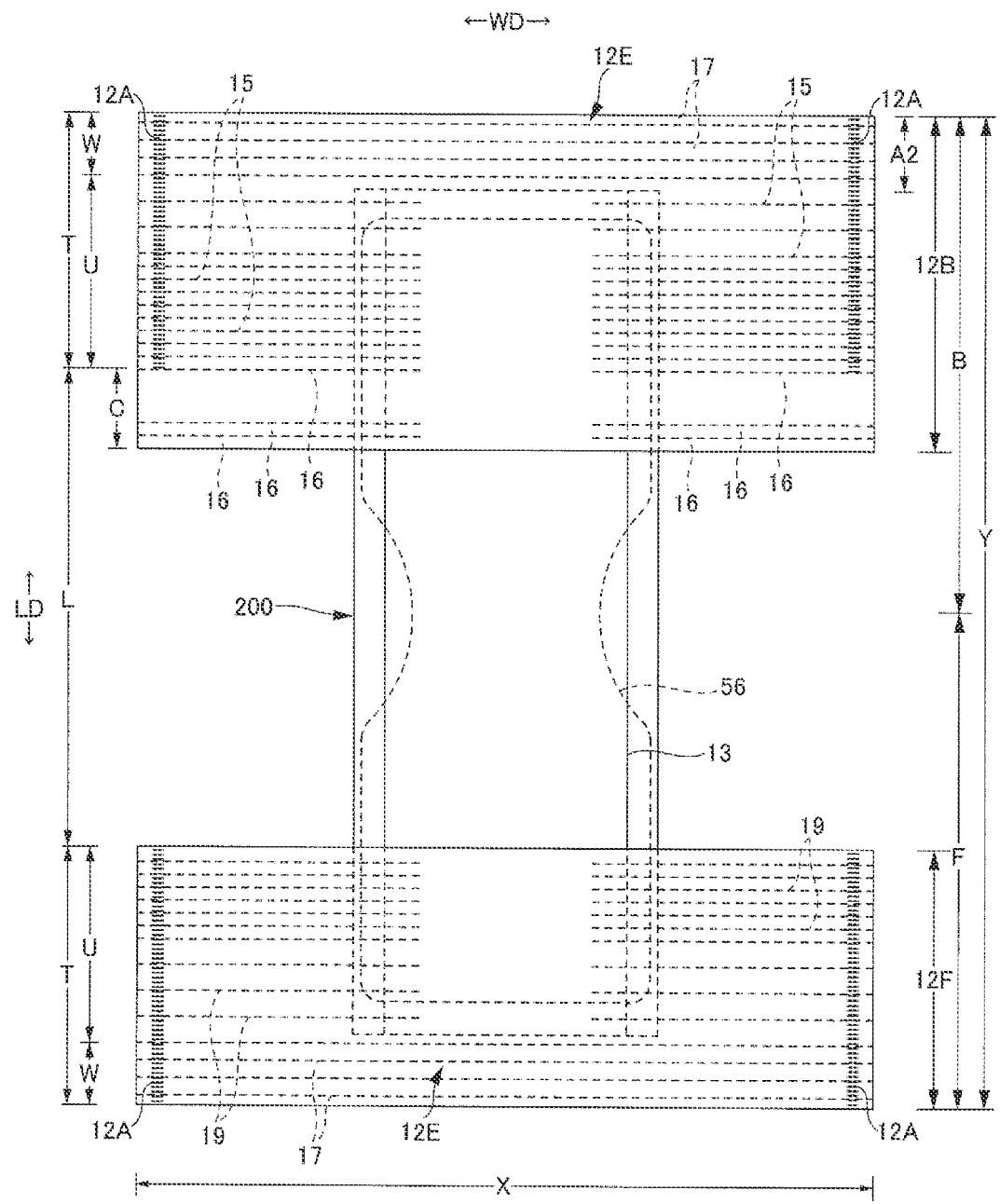
[FIG.2]

[FIG.3]
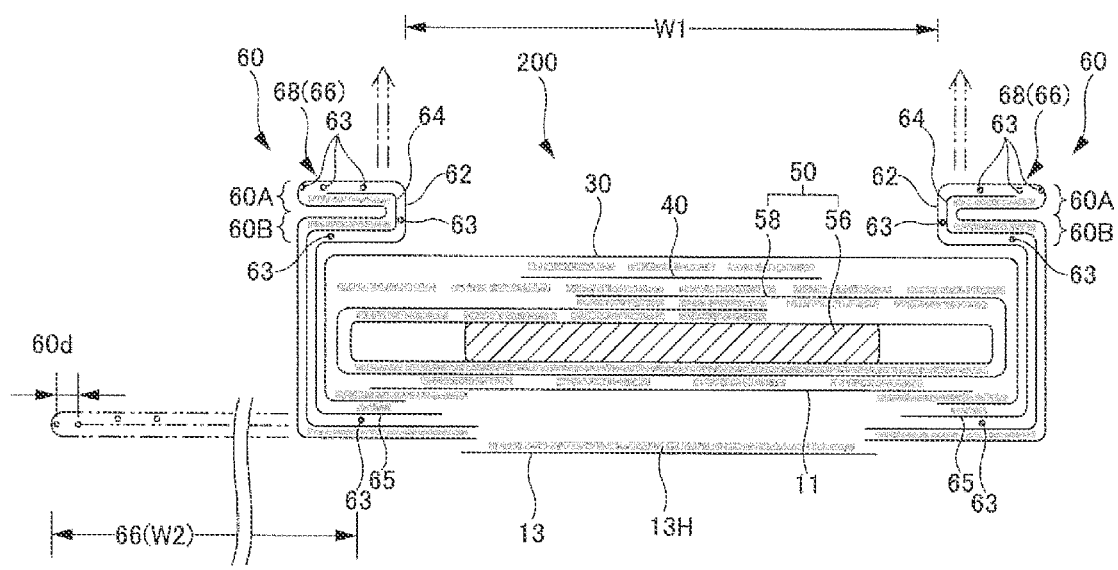

[FIG.4]
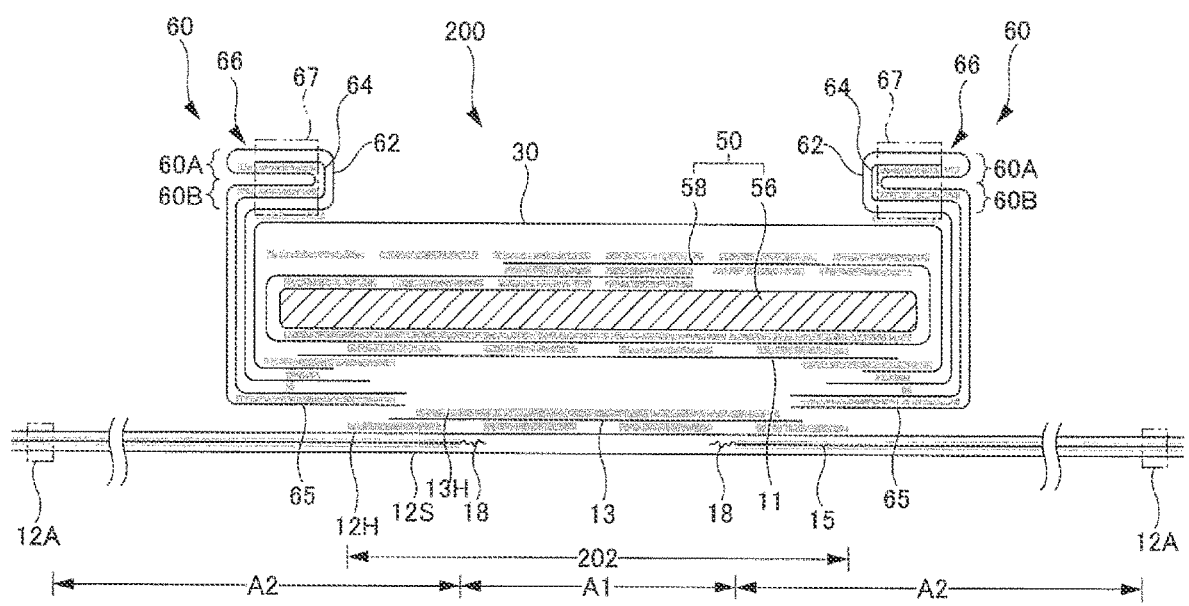

[FIG.5]
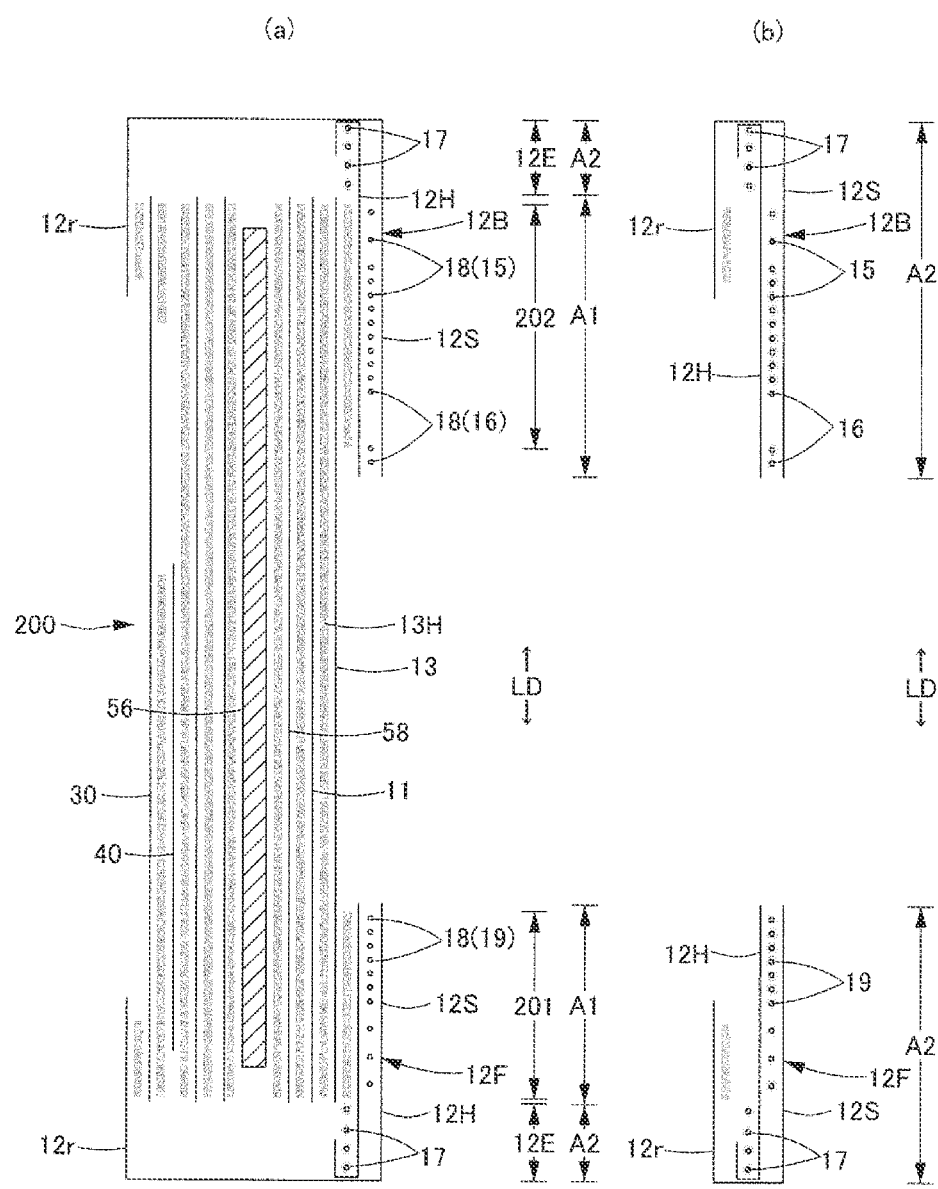

[FIG.6]
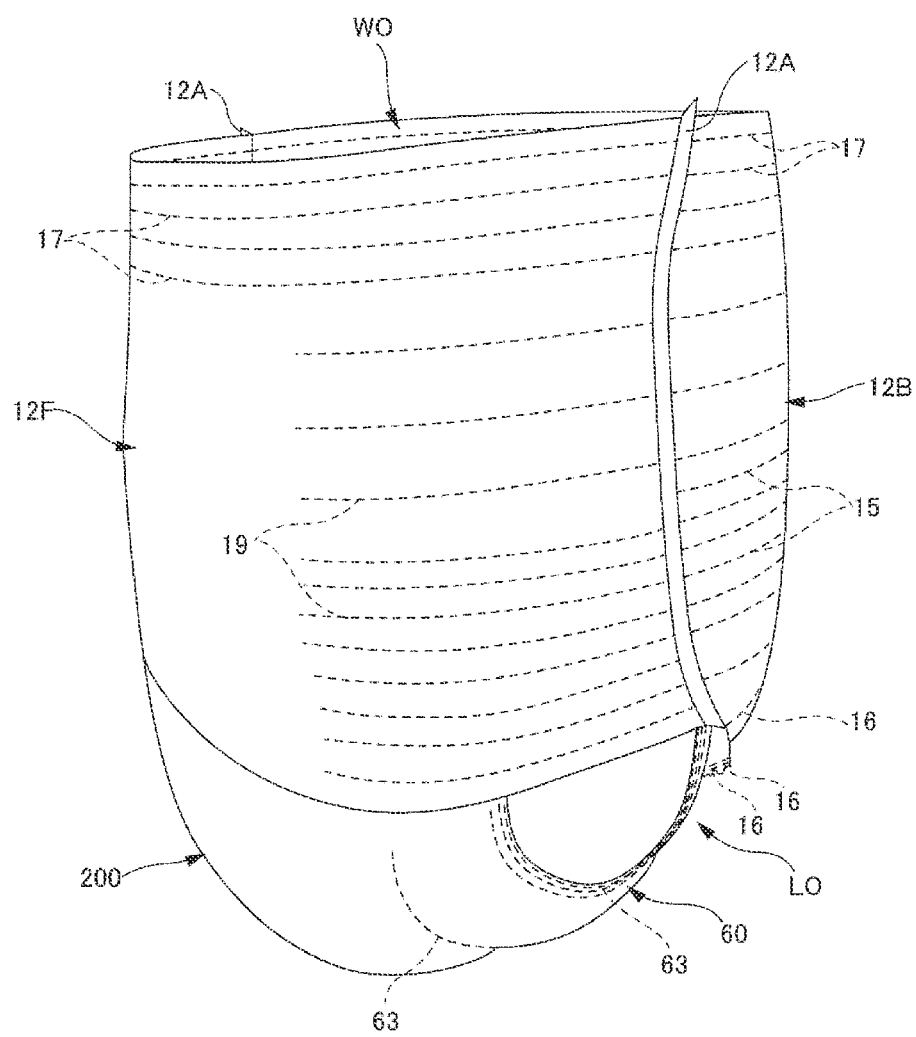

[FIG.7]
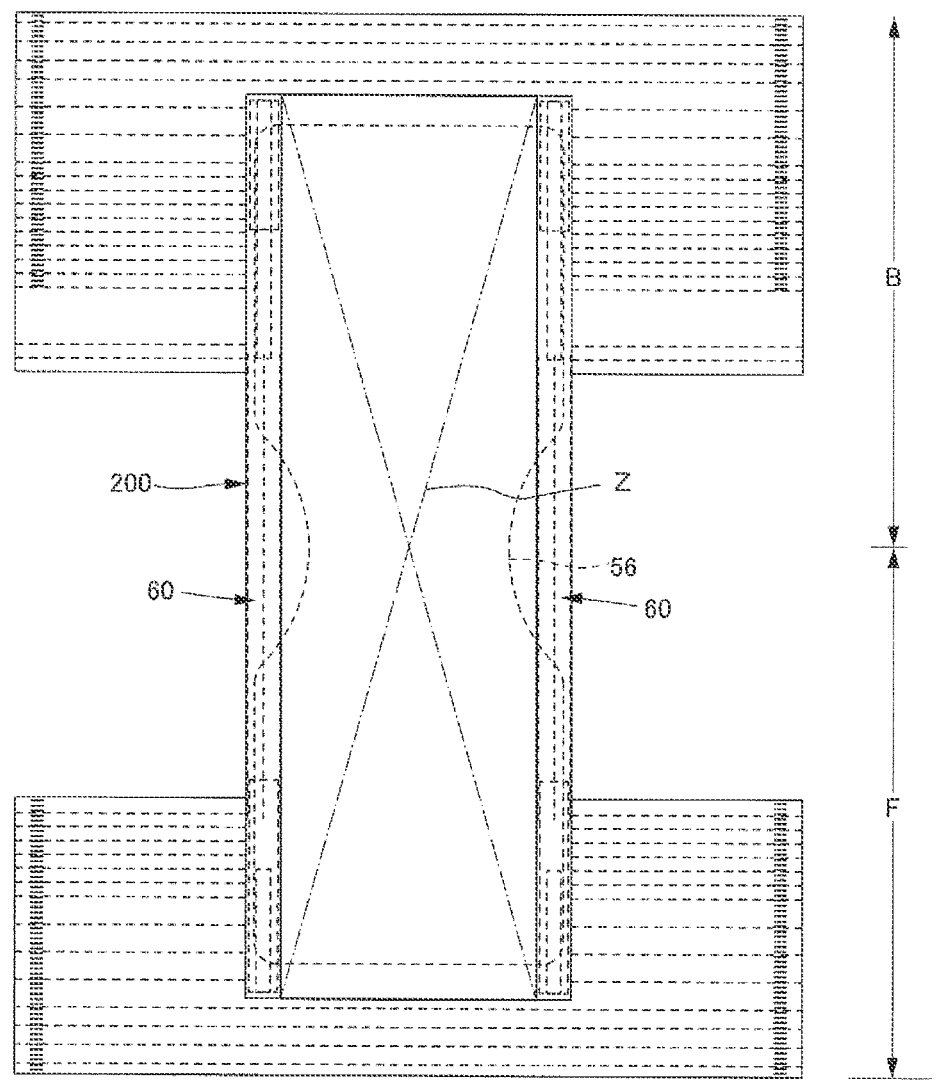

[FIG.8]
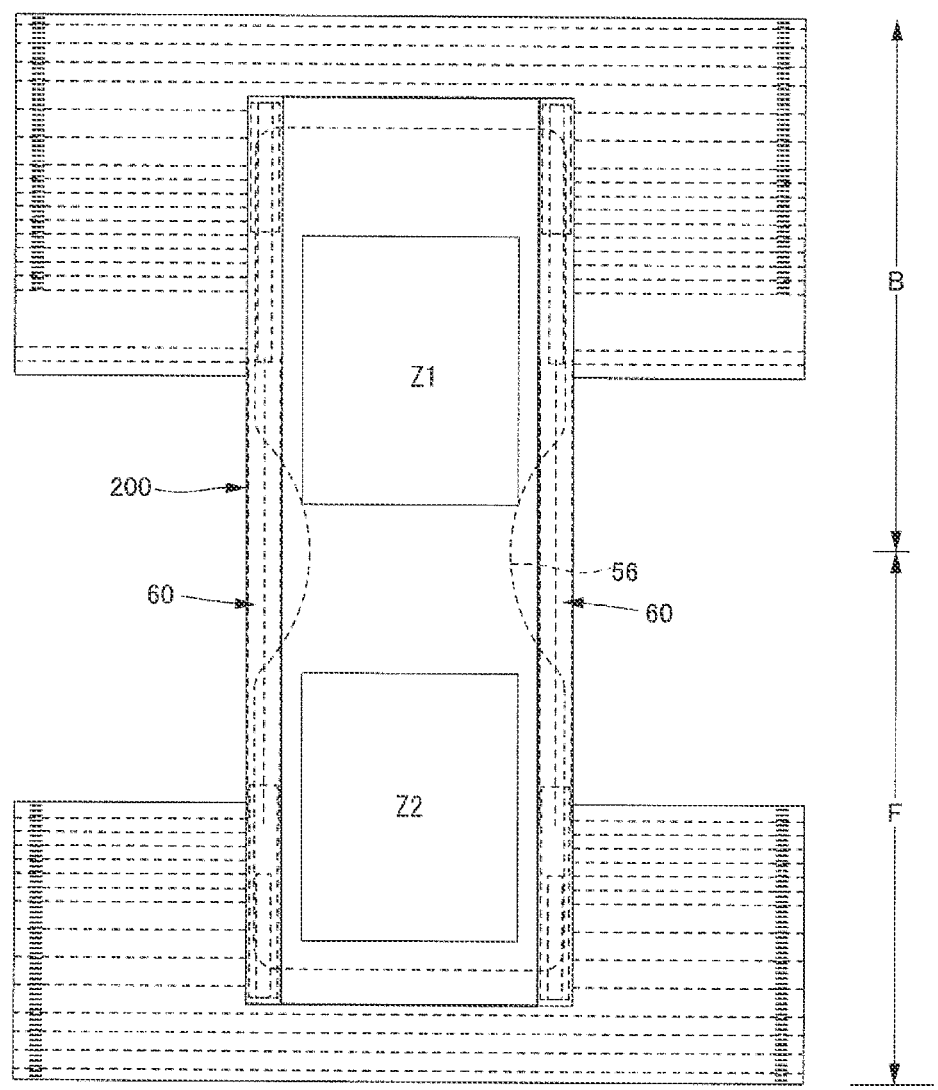

[FIG.9]
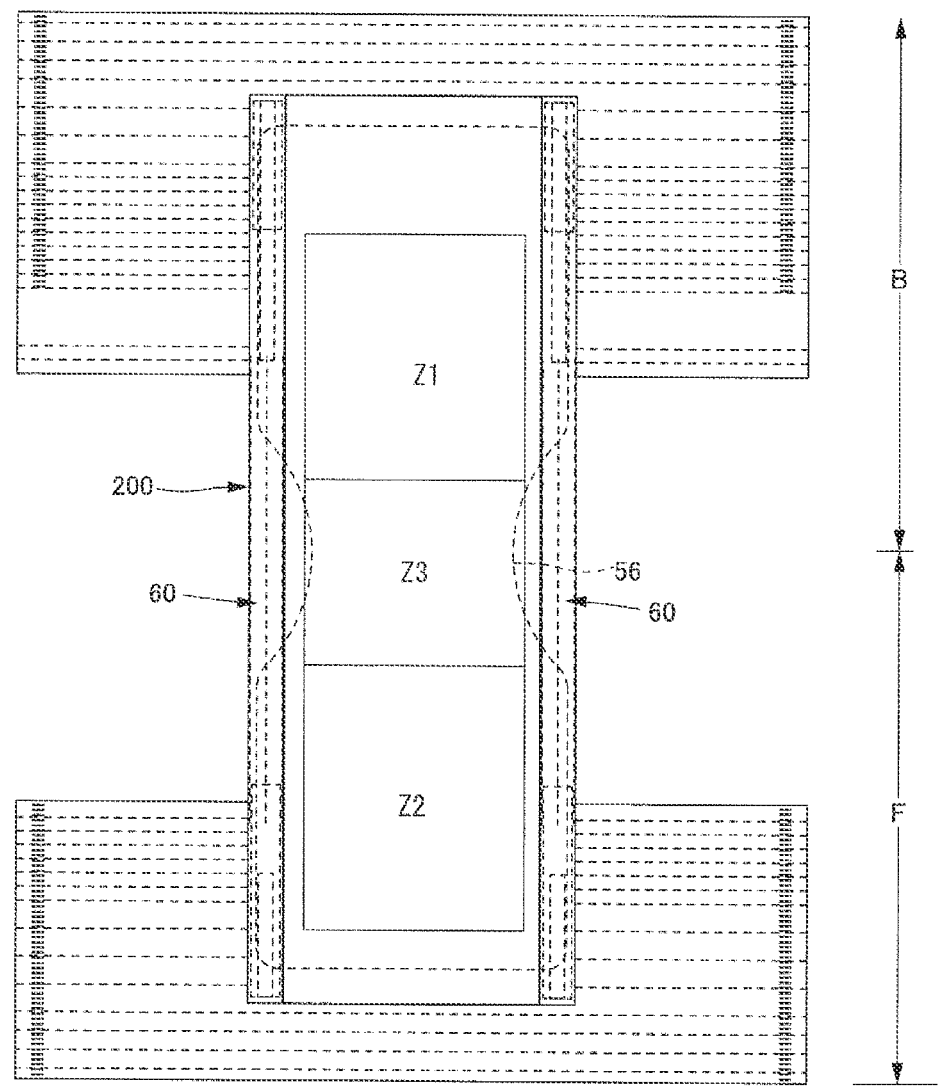

[FIG.10]
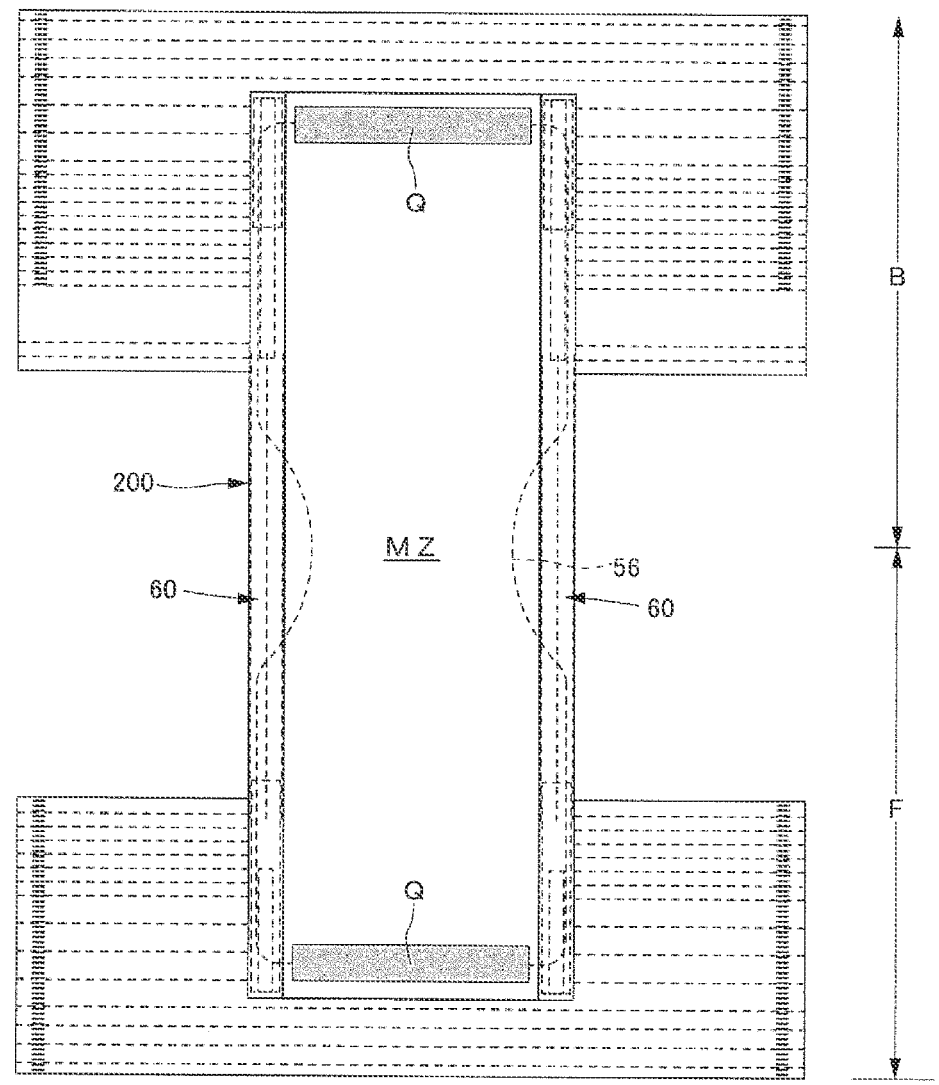

[FIG.11]
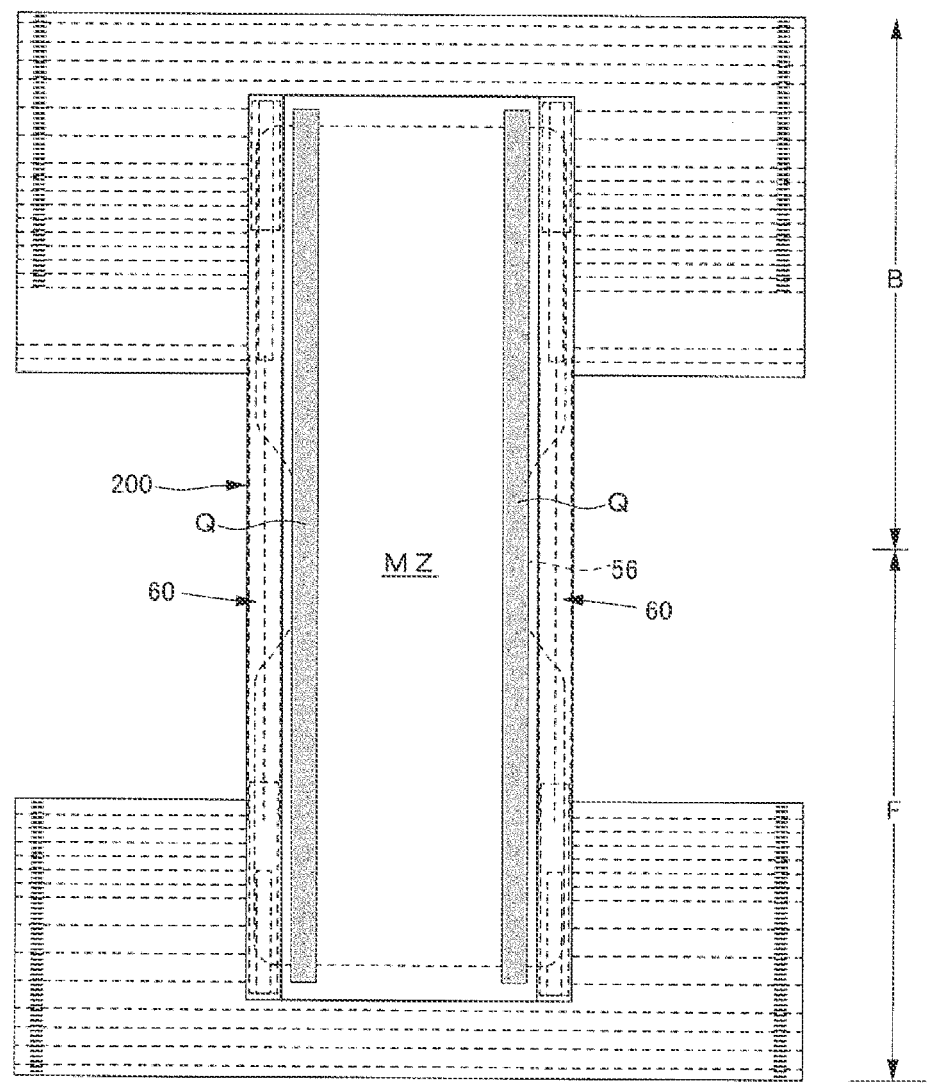

[FIG.12]
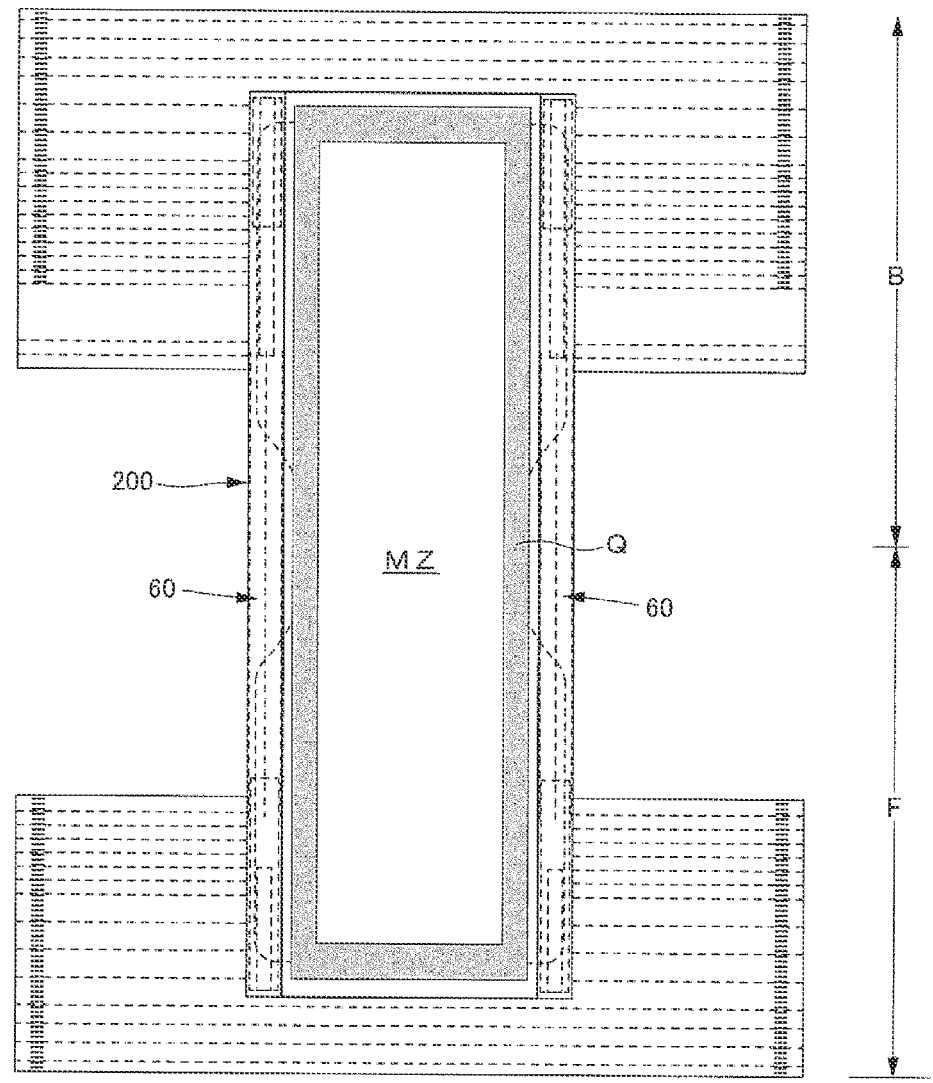

[FIG.13]
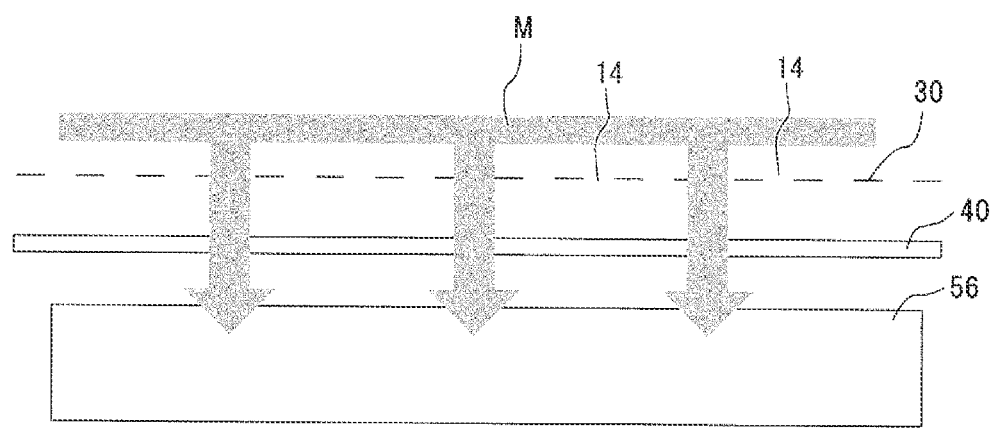

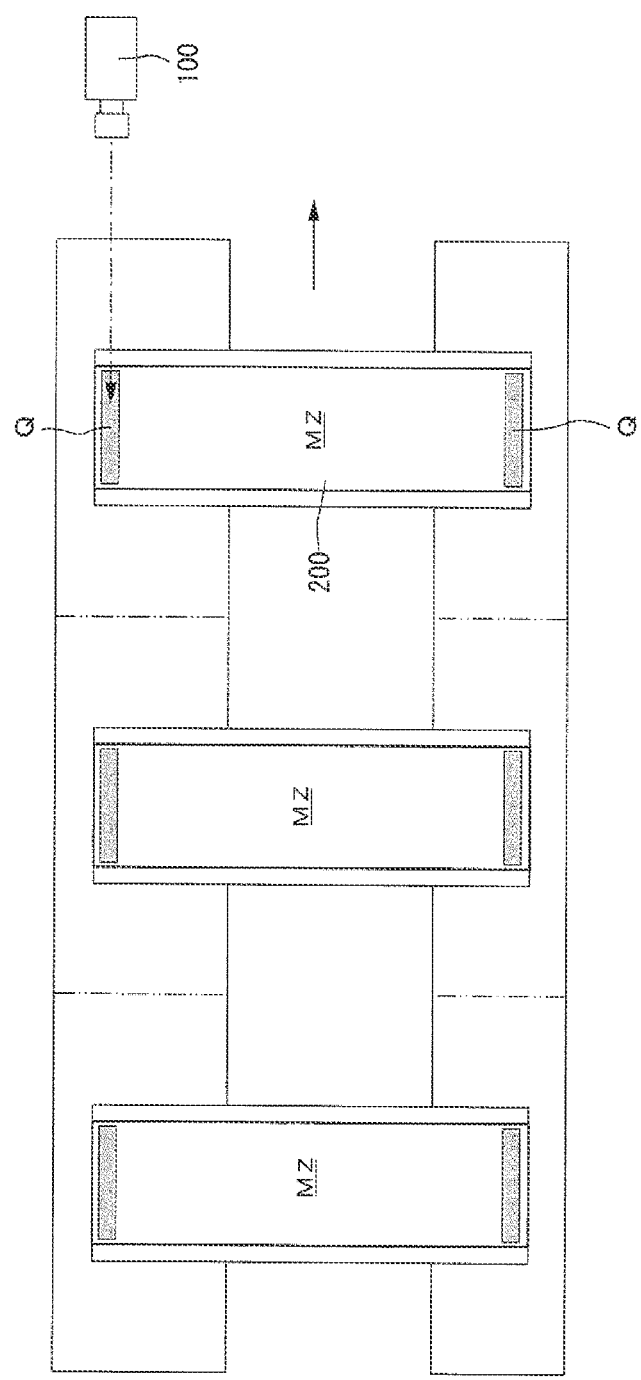

DISPOSABLE DIAPER AND METHOD FOR MANUFACTURING THE SAME

CROSS-REFERENCE TO RELATED APPLICATIONS

This application is the U.S. national stage application of International Application PCT/JP2021/017546, filed May 7, 2021, which international application was published on Dec. 2, 2021, as International Publication WO 2021/241169 in the Japanese language. The International Application claims priority of Japanese Patent Application No. 2020-091545, filed May 26, 2020. The international application and Japanese application are both incorporated herein by reference, in entirety.

TECHNICAL FIELD

The present invention relates to a disposable diaper and a method for manufacturing the same.

BACKGROUND ART

A disposable diaper often causes roughness of the skin of a wearer, particularly, rash disadvantageously.

Examples of a cause for this include friction with the skin at the time of wearing the diaper, and stimulation received by the skin from a body fluid and excreta (urine and loose stool) due to wearing the diaper for a long time.

In particular, the cause by stimulation due to contact of the skin with loose stool for a long time is large. In order to suppress this, the diaper needs to quickly absorb loose stool into an absorber. If the diaper can quickly absorb loose stool into the absorber, it is useful not only in reducing stimulation received by the skin but also in preventing leakage from a leg portion or a dorsal portion.

A first cause for hindering absorption of loose stool through a top sheet is that when loose stool passes through the top sheet, a loose stool component that cannot pass through the top sheet remains on a surface portion of fibers constituting the top sheet, and the top sheet is clogged. A second cause for hindering absorption of loose stool through the top sheet is that a defecation speed exceeds an absorption speed of the diaper, and loose stool cannot be absorbed and remains on the top sheet.

Therefore, it is very important for the diaper to quickly absorb loose stool into the absorber.

Patent Literature 1 discloses that a skin care agent, particularly a skin care agent containing a diamide derivative is disposed in a top sheet between so-called gather cuffs on both sides of a diaper in a width direction.

In particular, in a diaper worn by an infant, the skin of the infant is sensitive, and so-called diaper rash easily occurs.

CITATION LIST

Patent Literature

Patent Literature 1: JP 2018-102836 A

SUMMARY OF INVENTION

Technical Problem

In a case of obtaining a diaper in which a skin care agent for suppressing diaper rash is disposed, it is very important in terms of quality assurance to confirm whether or not the skin care agent is disposed in the product in a process of manufacturing the product.

Therefore, a main object of the present invention is to provide a disposable diaper capable of confirming whether or not a skin care agent, particularly a moisturizing agent is disposed in the product in a manufacturing process, and a method for manufacturing the disposable diaper.

Solution to Problem

A representative aspect of a disposable diaper solving the above problem is as follows.
<Representative Aspect of Disposable Diaper>
A disposable diaper including: a top sheet constituting a use-side surface; a liquid impervious sheet disposed on a back surface side; and an absorbent element interposed therebetween,
  wherein a moisturizing agent mainly containing glycerin is applied to the top sheet,
  an application region of the moisturizing agent is an exposed region that can be at least visually recognized directly from a use surface side in an unfolded state of the product, and
  the exposed region has high concentration application regions of the moisturizing agent in at least one of peripheral portions in a front-back direction and peripheral portions in a width direction, and a low concentration application region of the moisturizing agent in an intermediate region between the high concentration application regions.

A representative aspect of a method for manufacturing a disposable diaper is as follows.
<Representative Aspect of Method for Manufacturing Disposable Diaper>
A method for manufacturing a disposable diaper including a top sheet constituting a use-side surface, a liquid impervious sheet disposed on a back surface side, and an absorbent element interposed therebetween, the method including:
  applying a moisturizing agent mainly containing glycerin to the top sheet; and
  confirming whether or not the moisturizing agent is applied,
  wherein an application region of the moisturizing agent is an exposed region that can be at least visually recognized directly from a use surface side in an unfolded state of the product,
  the exposed region has high concentration application regions of the moisturizing agent in at least one of peripheral portions in a front-back direction and peripheral portions in a width direction, and a low concentration application region of the moisturizing agent in an intermediate region between the high concentration application regions, and
  in the confirming, the high concentration application regions are imaged using a near-infrared camera, and it is confirmed whether or not the moisturizing agent is present based on a level of a density of the obtained image.

Advantageous Effects of Invention

According to the present invention, it is possible to confirm whether or not a skin care agent, particularly a moisturizing agent is disposed in the product in a manufacturing process.

BRIEF DESCRIPTION OF DRAWINGS

FIG. 1 is a plan view illustrating an inner surface of an underpants-type disposable diaper in an unfolded state.

FIG. 2 is a plan view illustrating an outer surface of the underpants-type disposable diaper in an unfolded state.

FIG. 3 is a cross-sectional view cut along line 2-2 of FIG. 1.

FIG. 4 is a cross-sectional view cut along line 3-3 of FIG. 1.

FIG. 5(a) is a cross-sectional view cut along line 4-4 of FIG. 1, and FIG. 5(b) is a cross-sectional view cut along line 5-5 of FIG. 1.

FIG. 6 is a perspective view of the underpants-type disposable diaper.

FIG. 7 is a plan view for explaining an exposed region that can be visually recognized directly from a use surface side in an unfolded state of a product.

FIG. 8 is a plan view of an example of an application form of a moisturizing agent.

FIG. 9 is a plan view of another example of the application form of the moisturizing agent.

FIG. 10 is a plan view of an example of a high concentration application region of the moisturizing agent.

FIG. 11 is a plan view of an example of the high concentration application region of the moisturizing agent.

FIG. 12 is a plan view of an example of the high concentration application region of the moisturizing agent.

FIG. 13 is an explanatory diagram of permeation of the moisturizing agent.

FIG. 14 is an explanatory diagram of an aspect in which the high concentration application region of the moisturizing agent is imaged by a near-infrared camera.

DESCRIPTION OF EMBODIMENTS

Hereinafter, an embodiment of the present invention will be described in detail with reference to the attached drawings. A dotted pattern portion in the cross-sectional views illustrates an adhesive as a bonding means for bonding constituent members located on a front surface side and a back surface side, and is formed by applying a hot melt adhesive by solid application, bead application, curtain application, summit application, spiral application, pattern coating (transfer of a hot melt adhesive by a letterpress method), or the like. A fixing portion of an elastic member is formed, instead of this or in addition to this, by application to an outer peripheral surface of an elastic member by a comb gun, SureWrap application, or the like. Examples of the hot melt adhesive include an EVA-based agent, a pressure sensitive adhesive rubber-based agent (elastomer-based agent), a polyolefin-based agent, and a polyester/polyamide-based agent, and these can be used without particular limitation. As a bonding means for bonding constituent members, a means by material welding such as heat sealing or ultrasonic sealing can also be used.

FIGS. 1 to 6 illustrate an example of an underpants-type disposable diaper. The present underpants-type disposable diaper includes a rectangular front outer member 12F constituting at least a lower torso portion of a front body F, a rectangular back outer member 12B constituting at least a lower torso portion of a back body B, and an inner member 200 disposed inside the outer members 12F and 12B so as to extend from the front outer member 12F to the back outer member 12B via a crotch portion.

By bonding both sides of the front outer member 12F to both sides of the back outer member 12B to form side seal portions 12A, an opening formed by front and back end portions of the outer members 12F and 12B becomes a waist opening WO through which the torso of a wearer passes, and a portion surrounded by lower edges of the outer members 12F and 12B and a side edge of the inner member 200 on each side of the inner member 200 in a width direction becomes a leg opening LO through which the leg passes. The inner member 200 is a portion for absorbing and holding excrement such as urine, and the outer members 12F and 12B are portions for supporting the inner member 200 with respect to the body of a wearer. A reference character Y represents the maximum length of the diaper in an unfolded state (front-back direction length from an edge of the waist opening WO of the front body F to an edge of the waist opening WO of the back body B), and a reference character X represents the maximum width of the diaper in an unfolded state.

The underpants-type disposable diaper in the present embodiment has a lower torso region T defined as a front-back direction range (front-back direction range from the waist opening WO to an upper end of the leg opening LO) having the side seal portion 12A, and an intermediate region L defined as a front-back direction range of a portion forming the leg opening LO (between a front-back direction region having the side seal portion 12A of the front body F and a front-back direction region having the side seal portion 12A of the back body B). The lower torso region T can be divided into a "waist portion" W conceptually forming an edge of the waist opening and an "under-waist portion" U which is a portion lower than the waist portion W. Usually, in a case where the lower torso region T has a boundary in which a stretching stress in a width direction WD changes (for example, the fineness of an elastic member or the stretch rate thereof changes), a portion closer to the waist opening WO than the boundary closest to the waist opening WO is the waist portion W. In a case where there is no such a boundary, a waist extended portion 12E extending so as to be closer to the waist opening WO than an absorber 56 or the inner member 200 is the waist portion W. The front-back direction length varies depending on the size of a product and can be appropriately determined. For example, the length of the waist portion W can be 15 to 40 mm, and the length of the under-waist portion U can be 65 to 120 mm. Meanwhile, both side edges of the intermediate region L are each narrowed in a substantially U shape or a curved shape so as to follow a periphery of a wearer's leg, and the wearer's leg passes therethrough. As a result, the underpants-type disposable diaper in an unfolded state has an approximately hourglass shape as a whole.

(Inner Member)

The inner member 200 can adopt an arbitrary shape, but is rectangular in the illustrated form. As illustrated in FIGS. 3 to 5, the inner member 200 includes a top sheet 30 to become a body side, a liquid impervious sheet 11, and an absorbent element 50 interposed therebetween, and is a main unit section having an absorption function. A reference character 40 represents an intermediate sheet (second sheet) disposed between the top sheet 30 and the absorbent element 50 in order to rapidly transfer a liquid that has passed through the top sheet 30 to the absorbent element 50. A reference character 60 represents a side gather 60 extending so as to come into contact with a periphery of a wearer's leg from both sides of the inner member 200 in order to prevent leakage of excrement into both sides of the inner member 200.

(Top Sheet)

The top sheet 30 transmits a liquid, and examples thereof include a perforated or imperforated nonwoven fabric and a porous plastic sheet. Among these materials, the nonwoven fabric is not particularly limited concerning a raw material fiber thereof. Examples thereof include a synthetic fiber such as a polyolefin-based fiber including polyethylene and polypropylene, a polyester-based fiber, or a polyamide-based fiber, a regenerated fiber such as rayon or cupra, a natural fiber such as cotton, and a mixed fiber and a composite fiber in which two or more kinds of these fibers are used. Furthermore, the nonwoven fabric may be manufactured by any processing. Examples of a processing method include known methods such as a spunlacing method, a spunbonding method, a thermal bond method, a melt blown method, a needle punching method, an air through method, and a point bond method. For example, if softness and drapeability are demanded, a spunbonding method and a spunlacing method are preferable processing methods. If bulkiness and softness are demanded, an air through method, a point bond method, and a thermal bond method are preferable processing methods.

The top sheet 30 may be formed of a single sheet or a laminated sheet obtained by sticking two or more sheets to each other. Similarly, the top sheet 30 may be formed of a single sheet or two or more sheets in a plane direction.

Both sides of the top sheet 30 may be folded back to a back surface side at a side edge of the absorbent element 50 or may protrude from the side edge of the absorbent element 50 to a lateral side without being folded back.

For the purpose of preventing positional deviation with respect to a back surface side member or the like, it is desirable that the top sheet 30 is fixed to a member adjacent to the back surface side by a bonding means by material welding such as heat sealing or ultrasonic sealing, or with a hot melt adhesive. In the illustrated example, the top sheet 30 is fixed to a surface of the intermediate sheet 40 and a surface of a portion located on a front surface side of the absorber 56 in a wrapping sheet 58 with a hot melt adhesive applied to a back surface thereof.

(Intermediate Sheet)

In order to rapidly transfer a liquid that has passed through the top sheet 30 to the absorber, it is possible to dispose the intermediate sheet (also referred to as "second sheet") 40 having a higher liquid permeation speed than the top sheet 30. The intermediate sheet 40 is used in order to rapidly transfer a liquid to the absorber to enhance absorption performance of the absorber, and to prevent a "returning" phenomenon of the absorbed liquid from the absorber. The intermediate sheet 40 can be omitted.

Examples of the intermediate sheet 40 include a similar material to that of the top sheet 30, a spunlaced nonwoven fabric, a spunbonded nonwoven fabric, an SMS nonwoven fabric, a pulp nonwoven fabric, a mixed sheet of pulp and rayon, a point bonded nonwoven fabric, and crepe paper. In particular, an air through nonwoven fabric is preferable because of being bulky. As the air through nonwoven fabric, a composite fiber having a core-sheath structure is preferably used. In this case, a resin used for the core may be polypropylene (PP) but is preferably polyester (PET) having high rigidity. The basis weight is preferably 17 to 80 g/m$^2$, and more preferably 25 to 60 g/m$^2$. A raw material fiber of the nonwoven fabric preferably has a fineness of 2.0 to 10 dtex. In order to make the nonwoven fabric bulky, as mixed fibers of all or a part of raw material fibers, eccentric fibers having no core in the center, hollow fibers, eccentric and hollow fibers are also preferably used.

The intermediate sheet 40 in the illustrated example is disposed at the center so as to be shorter than the width of the absorber 56, but may be disposed over the maximum width. The front-back direction length of the intermediate sheet 40 may be the same as the maximum length of the diaper, may be the same as the length of the absorbent element 50, or may be within a short length range centered on a liquid receiving region.

For the purpose of preventing positional deviation with respect to a back surface side member or the like, it is desirable that the intermediate sheet 40 is fixed to a member adjacent to the back surface side by a bonding means by material welding such as heat sealing or ultrasonic sealing, or with a hot melt adhesive. In the illustrated example, the intermediate sheet 40 is fixed to a surface of a portion located on a front surface side of the absorber 56 in the wrapping sheet 58 with a hot melt adhesive applied to a back surface thereof.

(Liquid Impervious Sheet)

A material of the liquid impervious sheet 11 is not particularly limited, but examples thereof include a plastic film formed of a polyolefin-based resin such as polyethylene or polypropylene, a laminated nonwoven fabric having a plastic film disposed on a surface of a nonwoven fabric, and a laminated sheet obtained by superposing and bonding a nonwoven fabric or the like to a plastic film. For the liquid impervious sheet 11, it is preferable to use a liquid impervious and moisture permeable material favorably used from a viewpoint of preventing stuffiness. As a moisture pervious plastic film, a microporous plastic film obtained by kneading an inorganic filler and a polyolefin-based resin such as polyethylene or polypropylene, molding the kneaded mixture into a sheet, and then stretching the sheet in a monoaxial or biaxial direction is widely used. In addition, a nonwoven fabric using a micro denier fiber, a nonwoven fabric that has reinforced leakproofness by reducing a space between fibers by applying heat and pressure, and a sheet that has become liquid impervious without using a plastic film by a method for applying a super absorbent polymer, a hydrophobic resin, or a water repellent agent can be used as the liquid impervious sheet 11. However, it is desirable to use a resin film in order to obtain sufficient bonding strength at the time of bonding to a cover nonwoven fabric 13 described later through a hot melt adhesive.

The liquid impervious sheet 11 may have a width housed in a back surface side of the absorbent element 50 as illustrated in the drawing, or may go around both sides of the absorbent element 50 and extend to both sides of a side surface of the top sheet 30 of the absorbent element 50 in order to enhance leakproofness. The extending portion appropriately has a width of about 5 to 20 mm on each of the left and the right.

On an inner side of the liquid impervious sheet 11, in particular, on a side surface of the absorber 56, an excretion indicator that changes a color due to absorption of a liquid can be disposed.

(Side Gather)

The side gather 60 extends along both sides of the inner member 200 over the entire front-back direction LD, is disposed in order to prevent side leakage by being in contact with the periphery of a wearer's leg, and includes what is generally called a three-dimensional gather or a plane gather.

The side gather 60 illustrated in FIGS. 1, 3, and 4 is a so-called three-dimensional gather, and rises from a side of the inner member 200 to a front surface side. In the side gather 60, a root side portion 60B rises obliquely toward the center in the width direction, and a tip side portion 60A of the intermediate portion rises obliquely outward in the width direction. However, the side gather 60 is not limited thereto, and can be changed appropriately. For example, the side gather 60 can rise toward the center in the width direction as a whole.

More specifically, the side gather 60 in the illustrated example is formed by folding back a belt-shaped gather nonwoven fabric 62 having a length equal to the front-back direction length of the inner member 200 in the width direction WD at a tip portion to be folded in two, and fixing a plurality of elongated gather elastic members 63 to the folded portion and between the sheets near the folded portion in a stretched state in a longitudinal direction at intervals in the width direction WD. A base portion of the side gather 60 opposite to a tip portion thereof (an end portion opposite to the sheet-folded portion in the width direction WD) is a root portion 65 fixed to a side of a back surface side of the liquid impervious sheet 11 in the inner member 200, and a portion other than the root portion 65 is a main unit portion 66 (portion on the folded portion side) extending from the root portion 65. The main unit portion 66 has the root side portion 60B extending toward the center in the width direction, and the tip side portion 60A folded back at a tip of the root side portion 60B and extending outward in the width direction. In this form, the surface contact type side gather 60 is adopted. However, a line contact type side gather 60 not folded back outward in the width direction can also be adopted. Front-back direction both end portions of the main unit portion 66 are fallen portions 67 fixed to a side surface of the top sheet 30 in a fallen state. Meanwhile, a front-back direction intermediate portion located therebetween is a non-fixed free portion 68. The gather elastic member 63 in the front-back direction LD is fixed in a stretched state at least to a tip portion of the free portion 68.

In the side gather 60 configured as described above, a contraction force of the gather elastic member 63 acts so as to bring the front-back direction both end portions closer to each other. However, the front-back direction both end portions of the main unit portion 66 are fixed so as not to rise, whereas a portion therebetween is the non-fixed free portion 68. Therefore, only the free portion 68 rises so as to come into contact with a body side as illustrated by the arrow in FIG. 3. In particular, when the root portion 65 is located on a back surface side of the inner member 200, the free portion 68 rises so as to open outward in the width direction at a crotch portion and in the vicinity thereof. Therefore, the side gather 60 comes into contact with a periphery of a leg with a surface to improve fitting.

Like the side gather 60 in the illustrated example, in a bent form in which the main unit portion 66 includes the root side portion 60B extending toward the center in the width direction and the tip side portion 60A folded back at a tip of the root side portion 60B and extending outward in the width direction, the tip side portion 60A is bonded to the root side portion 60B in a fallen state at the fallen portion 67, and the root side portion 60B is bonded to the top sheet 30 in a fallen state. For bonding facing surfaces to each other in the fallen portion 67, at least one of a hot melt adhesive by various application methods and a means by material welding such as heat sealing or ultrasonic sealing can be used. In this case, bonding of the root side portion 60B to the top sheet 30 and bonding of the tip side portion 60A to the root side portion 60B may be performed by the same means or by different means. For example, it is one preferable form to bond the root side portion 60B to the top sheet 30 with a hot melt adhesive, and to bond the tip side portion 60A to the root side portion 60B by material welding.

(Absorbent Element)

The absorbent element 50 includes the absorber 56 and the wrapping sheet 58 wrapping the entire absorber 56. The wrapping sheet 58 can also be omitted.

(Absorber)

The absorber 56 can be formed by an assembly of fibers. As this fiber assembly, in addition to those obtained by accumulating short fibers such as fluff pulps or synthetic fibers, a filament assembly obtained by opening a tow (fiber bundle) of synthetic fibers such as cellulose acetate as necessary can also be used. In a case where fluff pulp or a short fiber is accumulated, a fiber basis weight may be, for example, about 100 to 300 g/m$^2$. In a case of a filament assembly, a fiber basis weight may be, for example, about 30 to 120 g/m$^2$. In a case of a synthetic fiber, a fineness is, for example, 1 to 16 dtex, preferably 1 to 10 dtex, and more preferably 1 to 5 dtex. In a case of a filament assembly, the filament may be formed of a non-crimped fiber but is preferably formed of a crimped fiber. The degree of crimp of the crimped fibers may be, for example, about 5 to 75, preferably 10 to 50, and more preferably 15 to 50 per 2.54 cm. A uniformly crimped fiber is often used. In the absorber 56, super absorbent polymer particles are preferably dispersed and held.

The absorber 56 may have a rectangular shape. However, as illustrated in FIG. 7 and the like, the absorber 56 preferably is of an hourglass shape having a narrower portion 56N with a narrower width than front-back direction both sides thereof in a front-back direction intermediate portion because fitting of the absorber 56 itself and the side gather 60 to a periphery of a leg is improved.

The size of the absorber 56 can be determined appropriately as long as the absorber 56 extends to the front, back, left, and right of a ureteral port position. However, the absorber 56 preferably extends to peripheral edges of the inner member 200 or the vicinity thereof in the front-back direction LD and the width direction WD. Note that a reference character 56X represents the maximum width of the absorber 56.

(Super Absorbent Polymer Particles)

The absorber 56 may contain super absorbent polymer particles partially or entirely. The super absorbent polymer particles include "powder" in addition to "particles". As super absorbent polymer particles 54, those used for this type of disposable diaper can be used as they are. For example, when sieving using a standard sieve of 500 μm (JIS Z8801-1: 2006) (shake for five minutes) is performed, particles in which a ratio of particles remaining on the sieve is 30% by weight or less are desirable. When sieving using a standard sieve of 180 μm (JIS Z8801-1: 2006) (shake for five minutes) is performed, particles in which a ratio of particles remaining on the sieve is 60% by weight or more are desirable.

(Wrapping Sheet)

In a case where the wrapping sheet 58 is used, as a material thereof, tissue paper, particularly, crepe paper, a nonwoven fabric, a polylaminated nonwoven fabric, a sheet with small holes, and the like can be used. However, it is desirable that the wrapping sheet 58 is a sheet from which super absorbent polymer particles do not escape. In a case where a nonwoven fabric is used instead of crepe paper, a hydrophilic SMS nonwoven fabric (SMS, SSMMS, or the like) is particularly suitable, and polypropylene, a polyethylene/polypropylene composite material, or the like can be used as a material thereof. A nonwoven fabric having a basis weight of 5 to 40 g/m$^2$, particularly of 10 to 30 g/m$^2$ is desirable.

A wrapping mode of the wrapping sheet 58 can be determined appropriately. However, a form is preferable in which the wrapping sheet 58 is wound around the absorber 56 cylindrically so as to surround front and back surfaces and both side surfaces of the absorber 56, the front and back end portions of the wrapping sheet 58 are caused to protrude from the front and back of the absorber 56, and a wound and overlapping portion and an overlapping portion of the front and back protruding portions are bonded with a hot melt adhesive or by a bonding means such as material welding from viewpoints of ease of manufacture, prevention of leakage of the super absorbent polymer particles from front and back edges, and the like.

(Outer Member)

The outer members 12F and 12B correspond to the rectangular front outer member 12F forming at least a lower torso portion of the front body F and the rectangular back outer member 12B forming at least a lower torso portion of the back body B, respectively. The front outer member 12F and the back outer member 12B are not continuous on a crotch side, and are separated from each other in the front-back direction LD. A separation distance thereof 12d can be about 150 to 250 mm, for example. The outer members 12F and 12B may be an integral outer member continuously extending from the front body F through a crotch to the back body B as described in Patent Literature 4.

The outer members 12F and 12B each have a lower torso portion which is a front-back direction range corresponding to the lower torso region T. In the present embodiment, the front-back direction size of the back outer member 12B is longer than that of the front outer member 12F, and the front outer member 12F does not have a portion corresponding to the intermediate region L, but the back outer member 12B has a gluteal cover portion C extending from the lower torso region T toward the intermediate region L.

The outer members 12F and 12B each include the elastic members 15 to 19 in order to enhance fitting of a wearer to a lower torso, thereby to form a stretchable region A2 that elastically stretches and contracts in the width direction WD along with stretching and contracting of the elastic members. In the stretchable region A2, in a natural length state, the outer members 12F and 12B contract along with contraction of an elastic member to form wrinkles or pleats. When the elastic member stretches in a longitudinal direction, it is possible to stretch the outer members 12F and 12B to a predetermined stretch rate at which the outer members 12F and 12B stretch without wrinkles. As the elastic members 15 to 19, in addition to an elongated elastic member (illustrated example) such as a rubber thread, a known elastic member such as a belt-shaped member, a net-shaped member, or a film-shaped member can be used without particular limitation. As the elastic members 15 to 19, either a synthetic rubber or a natural rubber may be used.

The elastic members 15 to 19 in the illustrated example will be described in more detail. In the waist portion W of each of the outer members 12F and 12B, a plurality of waist elastic members 17 is attached at intervals in the front-back direction so as to be continuous over the entire width direction WD. One or more waist elastic members 17 disposed in a region adjacent to the under-waist portion U may overlap with the inner member 200, or may be disposed on both sides thereof in the width direction except for the center region in the width direction overlapping with the inner member 200. As the waist elastic member 17, it is preferable to dispose 2 to 15 rubber threads, particularly 4 to 10 rubber threads each having a fineness of 155 to 1880 dtex, particularly about 470 to 1240 dtex (in a case of a synthetic rubber. A cross section area of 0.05 to 1.5 mm$^2$, particularly about 0.1 to 1.0 mm$^2$ in a case of a natural rubber) at intervals of 2 to 12 mm, particularly 3 to 7 mm. A stretch rate of the waist portion W in the width direction WD due to this is preferably 150 to 400%, and particularly preferably about 220 to 320%. In the waist portion W, all of the waist elastic members 17 in the front-back direction LD do not have to have the same fineness and the same stretch rate. For example, the fineness and the stretch rate of the elastic member 17 may be different between an upper portion and a lower portion of the waist portion W.

In the under-waist portion U of each of the outer members 12F and 12B, a plurality of under-waist elastic members 15 and 19 formed of an elongated elastic member is preferably disposed at intervals in the front-back direction. As the under-waist elastic members 15 and 19, it is preferable to dispose 5 to 30 rubber threads each having a fineness of 155 to 1880 dtex, particularly about 470 to 1240 dtex (in a case of a synthetic rubber. A cross section area of 0.05 to 1.5 mm$^2$, particularly about 0.1 to 1.0 mm$^2$ in a case of a natural rubber) at intervals of 1 to 15 mm, particularly 3 to 8 mm. A stretch rate of the under-waist portion U in the width direction WD due to this is preferably 200 to 350%, and particularly preferably about 240 to 300%.

In the gluteal cover portion C of the back outer member 12B, a cover portion elastic member 16 formed of an elongated elastic member is preferably attached. The gluteal cover portion C is contracted toward the center in the width direction WD by the cover portion elastic member 16. As the cover portion elastic member 16, it is preferable to dispose a rubber thread having a fineness of 155 to 1880 dtex, particularly about 470 to 1240 dtex (in a case of a synthetic rubber. A cross section area of 0.05 to 1.5 mm$^2$, particularly about 0.1 to 1.0 mm$^2$ in a case of a natural rubber). A stretch rate of the gluteal cover portion C in the width direction WD due to this is preferably 150 to 300%, and particularly preferably about 180 to 260%.

In the above example, the outer members 12F and 12B are separated from each other in the front-back direction, but may be continuous with each other (not illustrated).

(Moisturizing Agent and Application Thereof)

In order to maintain a skin condition of a wearer in a favorable state and to prevent diaper rash, it is desirable to apply a moisturizing agent to the top sheet 30 in a form such as an example described later.

As the moisturizing agent, those mainly containing glycerin are suitable. When the moisturizing agent is applied to an outer surface of the top sheet 30 (at least an outer surface portion of the top sheet 30 contains the moisturizing agent M), the moisturizing agent M protects the skin of a wearer.

Furthermore, the moisturizing agent M also has a function of reducing a frictional force with the skin of the wearer. As a result, when the disposable diaper is worn, the top sheet slides with respect to the skin according to a change in the posture of the wearer, contact with the skin of the wearer is secured, and a leakage preventing effect is enhanced.

The moisturizing agent mainly containing glycerin contains 70% by mass or more of glycerin as a component composition, and contains one or more additives selected from the group consisting of an emulsifier, a phosphate, a paraffin, and a surfactant as an additive as necessary. As the surfactant, an ether type nonionic surfactant and a nonionic surfactant containing an EO/PO type are preferable.

As schematically illustrated in FIG. 13, it is desirable that the top sheet 30 is a perforated nonwoven fabric in which a large number of openings 14 penetrating the nonwoven fabric from a front surface to a back surface are formed at intervals. When the top sheet 30 has openings 14 penetrating the nonwoven fabric from a front surface to a back surface, a loose stool component can be rapidly absorbed into the absorbent element 50 having the absorber 56 through the openings 14, which is useful not only for reducing stimulation received by the skin due to the loose stool component remaining on a surface of the top sheet 30 to suppress diaper rash but also for preventing leakage from a leg portion or a dorsal portion.

Under a common method for manufacturing a diaper, the moisturizing agent M is applied to the top sheet 30 by application or the like in a diaper manufacturing process, and then a large number of diaper products are compactly packaged. Due to this consolidation of a diaper, as schematically illustrated in FIG. 13, a part of the moisturizing agent M of the top sheet 30 is transferred to the intermediate sheet 40 through the openings 14.

The intermediate sheet generally has a higher body fluid permeation speed than the top sheet 30. In addition, the moisturizing agent M mainly containing glycerin has higher hydrophilicity than a hydrophilic diamide derivative. As a result, the moisturizing agent M that mainly contains glycerin and has been transferred to the intermediate sheet 40 side acts so as to draw in a body fluid from the top sheet 30 side or a loose stool component passing through the openings 14.

Therefore, the body fluid from the top sheet 30 side or the loose stool component passing through the openings 14 is rapidly guided to the absorbent element 50 side, and remaining of the body fluid such as a loose stool component on a surface of the top sheet 30 is suppressed. As a result, stimulation received by the skin is reduced, and diaper rash can be suppressed.

The moisturizing agent exhibits its function when being applied to a site in contact with the skin of a wearer. In the above embodiment, the site is a region between the side gathers 60 and 60 illustrated in FIG. 7. That is, the region between the side gathers 60 and 60 is an applicable region Z in the present invention.

In other words, the applicable region Z is an exposed region Z that can be visually recognized directly from a use surface side in an unfolded state of the product.

The moisturizing agent can be applied to an appropriate region in the applicable region (exposed region) Z. For example, as illustrated in FIG. 8, since the skin tends to be dry in a Z1 region on the back body B side where the gluteal region is located, the application amount of the moisturizing agent can be increased in the Z1 region, and since a Z2 region corresponding to the crotch portion tends to have a large amount of moisture, the application amount of the moisturizing agent can be reduced in the Z2 region.

That is, the low concentration application region has a plurality of application regions Z1 and Z2 having different concentrations of the moisturizing agent in the front-back direction.

Note that, regarding the application of the moisturizing agent to the top sheet 30, before the top sheet 30 is combined with another constituent material of the diaper, for example, before the top sheet 30 is combined with a constituent material of the side gather 60, the moisturizing agent can also be applied in a state of the top sheet 30 material. Therefore, for example, the moisturizing agent can also be applied in the maximum width of the top sheet 30 material beyond the applicable region (exposed region) Z in the width direction. Based on this point of view and the like, it has been clarified that the moisturizing agent is applied to an exposed region that can be "at least" visually recognized directly from a use surface side in an unfolded state of the product.

The crotch portion comes into contact with a loose stool component at a high frequency. In consideration that it is necessary to increase the application amount of the moisturizing agent in the crotch portion in order to cope with this, as illustrated in FIG. 9, the application amount in a central region Z3 can be larger (the concentration in the central region Z3 can be higher) than those in the back region Z1 and the front region Z2.

As a form in which the moisturizing agent is applied to the top sheet, an appropriate form such as non-contact type summit, spiral, signature, spray of one fluid or two fluids, a contact type slot coater, or a printing type hammer roll can be adopted.

On the one hand, when the application amount (concentration) of the moisturizing agent is increased, the moisturizing agent excessively adheres to the skin to make a wearer feel sticky, and there is a high possibility of giving discomfort to the wearer.

Therefore, there is an upper limit to the application amount of the moisturizing agent.

On the other hand, in a case of obtaining a diaper to which a moisturizing agent is applied, it is very important in terms of quality assurance (that is, in terms of defective product exclusion management) to confirm whether or not the moisturizing agent is applied to the product in a manufacturing process.

Since the moisturizing agent contains moisture, and the moisture absorbs light in a near-infrared wavelength region, for this confirmation, for example, it is conceivable to adopt a method for installing a near-infrared camera in a manufacturing line, imaging an application region of the moisturizing agent, and confirming whether or not the moisturizing agent is present based on a level of a density of the obtained image.

However, as a result of various experiments, it has been found that when the application amount of the moisturizing agent is small, a density difference in an image obtained by the near-infrared camera cannot be detected.

Therefore, when the application amount (concentration) of the moisturizing agent is increased such that a density difference in an image obtained by the near-infrared camera can be detected, the moisturizing agent excessively adheres to the skin to make a wearer feel sticky, and there is a high possibility of giving discomfort to the wearer.

In order to solve this problem, it has been found that high concentration application regions Q of the moisturizing agent are preferably formed in peripheral portions in the front-back direction and/or peripheral portions in the width direction in the exposed region (applicable region) Z (see FIG. 7), and the moisturizing agent is preferably applied at a low concentration in an intermediate region between the high concentration application regions Q and Q.

A reason for this is that even if the high concentration application region Q is present, this site is not a site where the moisturizing agent excessively adheres to the skin of a wearer to make the wearer feel sticky or uncomfortable.

For example, by adopting the forms illustrated in FIGS. 10 to 12, the high concentration application region Q can be imaged and detected by a near-infrared camera.

The example of FIG. 10 is an example in which the high concentration application regions (mark regions) Q are formed in the front and the back of the top sheet 30. The low concentration application region MZ of the moisturizing agent is located between the high concentration application regions (mark regions) Q and Q.

The example of FIG. 11 is an example in which the high concentration application regions (mark regions) Q are formed on the left and right side portions of the top sheet 30. The low concentration application region MZ of the moisturizing agent is located between the high concentration application regions (mark regions) Q and Q.

The example of FIG. 12 is an example in which the high concentration application regions (mark regions) Q are formed in the front, the back, the left, and the right of the top sheet 30. The low concentration application region MZ of the moisturizing agent is located in a region surrounded by the high concentration application regions (mark regions).

In the examples of FIGS. 10 to 12, in the low concentration application region in the exposed region (applicable region) Z, the moisturizing agent can be applied in the front-back direction at intervals in the width direction. In this form, since a manufacturing line flow direction and an application flow of the moisturizing agent coincide with each other, manufacture is easy.

FIG. 14 illustrates an outline of imaging the high concentration application region (mark region) Q. That is, for example, a near-infrared camera 100 is disposed in a manufacturing line in which a connection of semi-finished products of the disposable diaper of the application form of FIG. 10 is flowing laterally in the arrow direction (right direction), and the high concentration application region (mark region) Q is imaged.

The near-infrared ray is generally in a wavelength range of 780 nm to 2500 nm. Water absorbs light in a wavelength range of 1400 nm and 1900 nm. Therefore, detection by the near-infrared camera 100 is effective.

The present inventor performed the following experiments as to whether or not a skin care agent, particularly a moisturizing agent is disposed in a product, and performed various studies.

(1) A moisturizing agent containing glycerin is applied onto a surface material (hydrophilic air-through nonwoven fabric 18 g/m$^2$, 2.0/2.2 dtex) of an absorbent article by two-fluid spray and summit while an application concentration per unit area is changed.

The application concentrations were 0.1 g/m$^2$, 0.5 g/m$^2$, 2.0 g/m$^2$, 5 g/m$^2$, and 8.5 g/m$^2$.

(2) The sample is cut into a size of 5 cm×5 cm to prepare a test piece.

(3) Using a near-infrared camera (NIRCam-640SN) manufactured by Vision Sensing Co., Ltd., the test piece was irradiated with illumination (room light+external light from window) and photographed.

According to the above experiment, it has been found that the moisturizing agent can be detected and discriminated with sufficient sensitivity by the near-infrared camera 100 when the application concentration of the moisturizing agent is 8.5 g/m$^2$ (0.022 g/(5 cm×5 cm)) or higher.

In addition, according to 10 adult monitors, it has been found that when the application concentration is 15 g/m$^2$ (0.025 g/(5 cm×5 cm)) or higher, a sticky feeling is given.

It is desirable that the application amount is 0.02 to 0.04 g/5 cm×5 cm.

In the embodiment of the present invention, the low concentration application region MZ of the moisturizing agent is located in a region surrounded by the high concentration application regions (mark regions) Q.

In the low concentration application region MZ, it is desirable that the application concentration is 0.1 to 8.5 g/m$^2$. When the application concentration is excessively low, the effect of the moisturizing agent is not sufficient, and when the application concentration is excessively high, a sticky feeling is given.

On the other hand, it is desirable that a ratio regarding the moisturizing agent, the concentration of the high concentration application region (mark region) Q/the concentration of the low concentration application region MZ is 1.5 or more for discrimination.

<Explanation of Terms in Specification>

The following terms in the specification have the following meanings unless otherwise specified in the specification.

"Front-back (longitudinal) direction" means a direction connecting a ventral side (front side) and a dorsal side (back side), and "width direction" means a direction orthogonal to the front-back direction (left-right direction).

"Front surface side" means a side closer to a wearer's skin when an underpants-type disposable diaper is worn. "Back surface side" means a side far from a wearer's skin when an underpants-type disposable diaper is worn.

"Front surface" means a surface of a member closer to a wearer's skin when an underpants-type disposable diaper is worn. "Back surface" means a surface far from a wearer's skin when an underpants-type disposable diaper is worn.

"Stretch rate" means a value obtained when a natural length is 100%.

"Gel strength" is measured as follows. To 49.0 g of artificial urine (mixture of 2% by weight of urea, 0.8% by weight of sodium chloride, 0.03% by weight of calcium chloride dihydrate, 0.08% by weight of magnesium sulfate heptahydrate, and 97.09% by weight of deionized water), 1.0 g of a super absorbent polymer is added, and the resulting mixture is stirred with a stirrer. The gel thus generated is left in a thermohygrostat at 40° C.×60% RH for three hours. Thereafter, the temperature is returned to room temperature, and gel strength is measured with a curdmeter (Curdmeter-MAX ME-500 manufactured by I. Techno Engineering Co., Ltd.).

"Basis weight" is measured as follows. A sample or a test piece is predried and then left in a test chamber or an apparatus in a standard state (test location is at a temperature of 23±1° C. and a relative humidity of 50±2%) so as to have a constant weight. Predrying refers to causing a sample or a test piece to have a constant weight in an environment of a temperature of 100° C. Note that fibers having an official moisture regain of 0.0% do not have to be predried. A sample of 100 mm×100 mm in size is cut out from a test piece having a constant weight using a template for sampling (100 mm×100 mm). The weight of the sample is measured. The weight is multiplied by 10 to calculate the weight per square meter to be used as a basis weight.

"Thickness" is automatically measured under conditions that a load is 0.098 N/cm$^2$ and a pressing area is 2 cm$^2$ using an automatic thickness meter (KES-G5 handy compression measuring program).

Water absorption capacity is measured in accordance with JIS K7223-1996 "Test method for water absorption capacity of super absorbent polymer".

Water absorption speed is "time to end point" when JIS K7224-1996 "Test method for water absorption speed of super absorbent polymer" is performed using 2 g of super absorbent polymer and 50 g of physiological saline.

"Unfolded state" means a flatly unfolded state without contraction or slackness.

The size of each portion means a size not in a natural length state but in an unfolded state unless otherwise specified.

When environmental conditions in a test and a measurement are not described, the test and the measurement are performed in a test room or an apparatus in a standard state (test location is at a temperature of 23±1° C. and a relative humidity of 50±2%).

INDUSTRIAL APPLICABILITY

The present invention can be used not only for the underpants-type disposable diaper but also for a tape-type disposable diaper, a disposable pad used by being attached to a disposable diaper, and the like.

REFERENCE SIGNS LIST

11 Liquid impervious sheet
12A Side seal portion
12B Back outer member
12E Waist extended portion
12F Front outer member
12F, 12B Outer member
12H Second sheet material
12S First sheet material
13 Cover nonwoven fabric
15, 19 Under-waist elastic member
16 Cover portion elastic member
17 Waist elastic member
18 Unnecessary elastic member
200 Inner body
30 Top sheet
40 Intermediate sheet
50 Absorbent element
56 Absorber
58 Wrapping sheet
60 Side gather
62 Gather nonwoven fabric

The invention claimed is:

1. A method for manufacturing a disposable diaper including a top sheet constituting a use-side surface, a liquid impervious sheet disposed on a back surface side, and an absorbent element interposed therebetween, the method comprising:

applying a moisturizing agent mainly containing glycerin to the top sheet; and confirming whether or not the moisturizing agent is applied, wherein an application region of the moisturizing agent is an exposed region that can be at least visually recognized directly from a use surface side in an unfolded state of the product, the exposed region has high concentration application regions of the moisturizing agent in at least one of peripheral portions in a front-back direction and peripheral portions in a width direction, and a low concentration application region of the moisturizing agent in an intermediate region between the high concentration application regions, and in the confirming, the high concentration application regions are imaged using a near-infrared camera, and it is confirmed whether or not the moisturizing agent is present based on a level of a density of the obtained image.

* * * * *